US010344107B2

(12) United States Patent
Taylor et al.

(10) Patent No.: US 10,344,107 B2
(45) Date of Patent: Jul. 9, 2019

(54) ELECTRORESPONSIVE TECHNOLOGY

(71) Applicant: NORTH CAROLINA CENTRAL UNIVERSITY, Durham, NC (US)

(72) Inventors: Darlene K. Taylor, Durham, NC (US); Uddhav Balami, Durham, NC (US)

(73) Assignee: NORTH CAROLINA CENTRAL UNIVERSITY, Durham, NC (US)

( * ) Notice: Subject to any disclaimer, the term of this patent is extended or adjusted under 35 U.S.C. 154(b) by 415 days.

(21) Appl. No.: 15/034,359

(22) PCT Filed: Nov. 14, 2014

(86) PCT No.: PCT/US2014/065791
§ 371 (c)(1),
(2) Date: May 4, 2016

(87) PCT Pub. No.: WO2015/073882
PCT Pub. Date: May 21, 2015

(65) Prior Publication Data
US 2016/0289350 A1 Oct. 6, 2016

Related U.S. Application Data

(60) Provisional application No. 61/904,078, filed on Nov. 14, 2013.

(51) Int. Cl.
| | | |
|---|---|---|
| C07C 17/16 | (2006.01) | |
| C07C 29/147 | (2006.01) | |
| C07C 43/23 | (2006.01) | |
| C08F 8/36 | (2006.01) | |
| C08F 12/22 | (2006.01) | |
| C08F 12/30 | (2006.01) | |
| C08F 12/32 | (2006.01) | |
| G01N 27/327 | (2006.01) | |
| G01N 27/333 | (2006.01) | |

(52) U.S. Cl.
CPC ............. *C08F 12/30* (2013.01); *C07C 17/16* (2013.01); *C07C 29/147* (2013.01); *C07C 43/23* (2013.01); *C08F 8/36* (2013.01); *C08F 12/22* (2013.01); *C08F 12/32* (2013.01); *G01N 27/3277* (2013.01); *C07C 2603/90* (2017.05); *G01N 27/3335* (2013.01)

(58) Field of Classification Search
CPC .......... C08F 12/30; C08F 12/22; C08F 12/32; C08F 8/36; C07C 29/147; C07C 43/23; C07C 17/16; C07C 2603/90; G01N 27/3277; G01N 27/3335
See application file for complete search history.

(56) References Cited

U.S. PATENT DOCUMENTS

| 4,699,966 A | 10/1987 | Harris et al. | |
|---|---|---|---|
| 2008/0058443 A1 | 3/2008 | Moszner et al. | |
| 2010/0202960 A1* | 8/2010 | Enomura | B01F 3/12 423/612 |
| 2013/0266872 A1* | 10/2013 | Adamson | H01M 2/166 429/246 |

FOREIGN PATENT DOCUMENTS

| CN | 102304141 A | 1/2012 |
|---|---|---|
| WO | 2001/60774 | 8/2001 |

OTHER PUBLICATIONS

Alexandratos et al., "Synthesis and Ion-Binding Affinities of Calix[4]arenes Immobilized on Cross-Linked Polystyrene", American Chemical Society, 2001, pp. 206-210.*
Vikrant Saluja, et al., "Calixarenes and Cucurbiturils: Pharmaceutial and Biomedical Applications", J Pharm Educ Res, (Jun. 2013), vol. 4, No. 1, p. 16-25.
Ana R. Mendes, et al., "Linear and Crossrinked Copolymers of p-tert-butylcalix[4]arene Derivatives and Styrene: New Synthetic Approaches to Polymer-Bound Calix[4]arenes", Reactive & Functional Polymers, (2005), vol. 65, p. 9-21.
Dong-Sheng Guo, et al., "Highly Effective Binding of Methyl Viologen Dication and its Radical Cation by p-Sulfonatocalix[4,5]arenes", J. Org. Chem., (2007), vol. 72, p. 7775-7778.
P. Sreedevi, et al.,., "Studies on the Zetapotential of Calcite/p-Sulfonatocalix [4,8]arenes", Journal of Dispersion Science and Technology, (2011). vol. 32, p. 1531-1536.
European Search Report dated Apr. 18, 2017 for Application No. EP 14861287.2.
espacenet English abstract of CN 102304141 A.
Gungor, O., et al., "Synthesis of alkyl nitrile and alkyl benzonitrile derivatives of calix[4]arene and their polymer supported analogues: A comparative study in two-phase extraction systems", Reactive & Functional Polymers, vol. 63, No. 1, Apr. 1, 2005, pp. 1-9.
Balami, U., et al., "Electrochemical responsive arrays of sulfonatocalixarene groups prepared by free radical polymerization", Reactive & Functional Polymers, vol. 81, 2014, pp. 54-60.
C. David Gutsche, "Embroidering the Baskets: Modifying the Upper and Lower Rims of Calixarenes", Chapter 5, Calixarenes Revisited, 1998, 79-145.

(Continued)

*Primary Examiner* — Patrick D Niland
(74) *Attorney, Agent, or Firm* — Ladas & Parry LLP (57) ABSTRACT

A styrene based water soluble polymer containing pendant sulfonated calix[4]arene groups has been synthesized by using free radical polymerization combined with post-polymerization sulfonation chemistry. The monomer 25-(4-vinylbenzyl)-26, 27, 28-hydroxy-calix[4]arene was prepared in 3 steps: (1) reduction of 4-vinyl benzoic acid to the respective alcohol (2) formation of the bromide by the Appel reaction and (3) synthesis of the respective ether by Williamson O-alkylation reaction with calix[4]arene. Polymerization was accomplished by azobisisobutyronitrile (AIBN) initiated free radical polymerization technique. Electro-responsive properties of the sulfonated polymer were studied wherein a response to electrochemical stimulus is observed when guest molecules of methyl viologen are incorporated with polymerized 25-(4-vinylbenzyl)-26, 27, 28-hydroxy-calix[4]arene.

20 Claims, 11 Drawing Sheets

(56) References Cited

OTHER PUBLICATIONS

C. David Gutsche, "Filling the Baskets: Complex Formation with Calixarenes", Chapter 6, Calixarenes Revisited, 1998, 146-184.

Christopher W. Hall, et al., "Clean and efficient syntheses of calix[4]arene modified polymer supports", Green Chemistry, 2001, 3, 114-122.

Zhen-Lin Zhong, et al., "Synthesis and Properties of Calixcrown Telomers", J. Chem. Soc., Chem. Commun., 1995, 1737-1738.

Stephen J. Harris, et al., "Polymeric Calixarenes. Synthesis, Polymerisation and Na+, Complexation of a Calix[4]arene Methacrylate", J. Chem. Soc., Chem. Commun., 1991, 1224-1225.

Seiji Shinkai, et al., "Selective Adsorption of UO2+/2 to a Polymer Resin Immobilizing Calixarene-Based Uranophiles", Journal of Polymer Science: Part C: Polymer Letters, vol. 26, 391-396 (1988).

Michael T. Blanda, et al., "Syntheses and characterizations of two copolymers containing cone conformations of calix [4]arenes in the polymer backbone", Chem. Commun., 139-140, 1998.

Michael T. Blanda, et al., "Syntheses and characterizations of three vinyl copolymers containing pendant calix[4]arenes", Polymer vol. 39, No. 16, 1998, pp. 3821-3826.

Volker Bohmer, "Calixarenes, Macrocycles with (Almost) Unlimited Possibilities", Angew. Chem. Int. Ed. Engl. 1995, 34, 713-745.

Khushrav B. Crawford, "Na+ Specific Emission Changes in an Ionophoric Conjugated Polymer", J. Am. Chem. Soc. 1998, 120, 5187-5192.

D. M. Gravett, et al., "Synthesis and Photophysical Properties of a Novel Water-Soluble, Calixarene-Containing", Polymer, American Chemical Society, Macromolecules 1996, 29, 617-624.

Dong-Sheng Guo, et al., "Electrochemical stimulus-responsive supramolecular polymer based on sulfonatocalixarene and viologen dimers", The Royal Society of Chemistry, Chem. Commun., 2010, 46, 2620-2622, www.rsc.org/chemcomm.

Alexander Katz, et al., "The First Single-Step Immobilization of a Calix-[4]-arene onto the Surface of Silica", American Chemical Society, Chem. Mater. 2002, 14, 3364-3368.

Sang Il Kim, et al., "Synthesis and Characterization of New Polyimides Containing Calix[4]arenes in the Polymer Backbone", Journal of Polymer Science: Part A: Polymer Chemistry, vol. 37, 2013-2026 (1999).

Elzbieta Malinowska, et al., "Novel approach of immobilization of calix[4]arene type ionophore in 'self-plasticized' polymeric membrane", Analytica Chimica Acta 421 (2000) 93-101.

Ling-Zhi Meng, et al., "Preparation and Behavior of Calix[4]arene-containing Organosilicone Resins (I)", Journal of Applied Polymer Science, vol. 80, 58-64 (2001).

Wilma F. Nijenhuis, "Calixcrowns as Selective Potassium Cation Carriers in Supported Liquid Membranes", J. Am. Chem. Soc. 1991, 113, 7963-7968.

Pawel Parzuchowski, "Calix[4] arene derived tetraester receptors modified at their wide rim by polymerizable groups", New J., Chem., 1999, 23, 757-763.

Gulderen Uysal, "Synthesis and binding properties of polymeric calix[4]arene nitriles", Reactive & Functional Polymers 50 (2001) 77-84.

Aytan Yilmaz, et al., "Synthesis and Binding Properties of Calix[4]arene Telomers", Journal of Polymer Science: Part A: Polymer Chemistry, vol. 37, 4351-4355 (1999).

\* cited by examiner

Fluorescence observed after quenching P(VBSC4A) (20μM) by consecutive addition of multiple of 3.2 μM MV in PBS solution.

FIG. 9

Raw ITC data for sequential 20 injections of MV solution (2.00 mM) injecting into P(VBSC4A) (250μM) in aqueous solution (A). Apparent reaction heat obtained from the integration of calorimetric traces (B).

FIG. 10

CV curve of MV (1.5mM) and mixture of MV and P(VBSC4A) solution (1.5mM each, scan rate 200 mV/s) in PBS solution

FIG. 11

ELECTRORESPONSIVE TECHNOLOGY

CROSS-REFERENCE TO RELATED APPLICATION

This U.S. application claims priority under 35 U.S.C 371 to, and is a U.S. National Phase application of, the International Patent Application No. PCT/US2014/065791, filed 14 Nov. 2014, which claims priority from U.S. 61/904,078 filed 14 Nov. 2013, the disclosures of which are incorporated in their entirety by reference herein.

STATEMENT REGARDING FEDERALLY SPONSORED RESEARCH OR DEVELOPMENT

This invention was made, in part, with Government support from the National Science Foundation under Award Number DMR-1121107. The U.S. Government may have certain rights in this invention.

BACKGROUND OF THE INVENTION

Host-guest complexes based on calixarenes and neutral and ionic molecular guests as well as with metal ions have been investigated in solid and solution studies (C. D. Gutsehe, Calixarenes Revisited, first ed. Royal Society of Chemistry, The Cambridge, 1989; V. Bohmer, Angew. Chem., Int. Ed. Engl. 34 (1995), 713-745). As a class of materials, calixarenes form the key component for selective electrodes and membranes, chemical and biochemical sensors, and selective extraction of ions and neutral molecules (W. F. Nijenhuis, E. G. Buitenhuis, F. De Jong, E. J. R. Sudholter, D. N. Reinhoudt, J. Am. Chem. Soc 113 (1991) 7963-7968; D. Diamond, M. A. McKervey, Chem. Soc. Rev. 25 (1996) 15-24; K. B. Crawford, M. B. Goldfinger, T. M. Swager, J. Am. Chem. Soc 120 (1998) 5187-5192; S. I. Kim, T. J. Shin, M. Ree, G. T. Hwang, B. H. Kim, H. Han, J. Seo, J. Polym. Sci, Part A: Polym. Chem. 37 (1999) 2013-2026 and E. Malinowska, L. Gawart, P. Parzuchowski, G. Rokicki, Z. Brzozka, Anal. Chirsi, Acta 421 (2000) 93-101). D. S. Guo, S. Chen, H. Qian, H. Q. Zhang, Y. Lui, Chem. Commun. 46 (2010) 2620-2622 report of a main chain supramolecular polymer where the dynamic bonds are those supramolecular interactions between a bis-p-sulphonato-calix[4]arene and an electro-responsive bis-viologen. The viologen, in its oxidized state, binds to the calixarene moieties but does not interact as strongly with the negatively charged calixarenes in its reduced neutral state.

There have been reports focused on covalently bound calixarene main chain polymers (G. Uysal, et al., Synthesis and binding properties of polymeric calix [4] arene nitriles, Reactive and Functional Polymers 50 (2002) 77-84; A. Katz, et al., The First Single-Step Immobilization of a Calix-[4]-arene onto the Surface of Silica, Chemistry of Materials 14 (2002) 3364-3368; S. D. Alexandratos et al, Synthesis and Ion-Binding Affinities of Calix[4]arenes Immobilized on Cross-Linked Polystyrene, Macromolecules 34 (2000) 206-210; C. W. Hall, J. S. et al., Clean and efficient syntheses of calix[4]arene modified polymer supports, Green Chemistry 3 (2001) 114-122; K. Ohto, et al., Adsorptive Separation of Lead and Zinc Ions by Novel Type of Calix[4]arene Carboxylate Resin Immobilized with Polyallylamine, Chemistry Letters 26 (1997) 647-648; S. Shinkai et al., Selective adsorption of UO22+ to a polymer resin immobilizing calixarene-based uranophiles, Journal of Polymer Science Part C: Polymer Letters 26 (1988) 391-396; L.-Z. Meng, et al, Preparation and behavior of calix[4]arene-containing organosilicone resins (I), Journal of Applied Polymer Science 80 (2001) 58-64; A. Yilmaz, et al, Synthesis and binding properties of calix[4]arene telomers, Journal of Polymer Science Part A: Polymer Chemistry 37 (1999) 4351-4355; M. T, Blanda, et al., Syntheses and characterizations of two copolymers containing cone conformations of calix[4]arenes in the polymer backbone, Chemical Communications (1998) 139-140; Z.-L. Zhong, et al., Synthesis and properties of calixcrown telomers, Journal of the Chemical Society, Chemical Communications (1995) 1737-1738; P. Parzuchowski, et al, Calix[4]arene derived tetraester receptors modified at their wide rim by polymerizable groups, New Journal of Chemistry 23 (1999) 757-763; M. T. Blanda, E. et al., Syntheses and characterizations of three vinyl copolymers containing pendant calix[4]arenes, Polymer 39 (1998) 3821-3826; D. M. Gravett, et al, Synthesis and Photophysical Properties of a Novel Water-Soluble, Calixarene-Containing Polymer, Macromolecules 29 (1996) 617-624; and S. J. Harris, et al., Polymeric calixarenes. Synthesis, polymerisation and Na+ complexation of a calix[4]arene methacrylate, Journal of the Chemical Society, Chemical Communications (1991) 1224-1225.)

The references cited herein are hereby expressly incorporated by reference as fully as if their content had been set forth herein.

No report has focused on a sulfonated calixarene unit immobilized as a pendant electrochemically-responsive system on a polystyrene backbone.

There is a need to provide polymeric styrene based materials for reversibly binding materials.

A styrene-based polymer with pendant sulfonated calixarene has been synthesized. The polymer is sensitive to electrical stimuli as determined by its ability to reversibly bind a guest molecule.

SUMMARY OF THE INVENTION

An aspect of this invention relates to a sulfonated ealixarene unit immobilized as a pendant electrochemically-responsive system on a polystyrene backbone. Another aspect of this invention is a polystyrene based water soluble polymer with pendant sulfonocalixarene units.

The polymer is sensitive to electrical stimuli as determined by its ability to reversibly bind a guest molecule. Such a reversible binding system is useful in connection with the design of sophisticated polymeric materials with excellent responsive properties.

A further aspect of this invention is a method for making a polystyrene based water soluble polymer with pendant sulfonocalixarene units Another aspect of the invention is a styrene based water soluble monomer containing pendant ealixarene units.

An aspect of the invention is a styrene based water soluble polymer containing pendant ealixarene units.

These and other aspects and advantages of the invention will be apparent to those skilled in the art from the following description.

BRIEF DESCRIPTION OF THE FIGURES

FIG. 10(a) shows Raw ITC data for sequential 20 injections of MV solution (2.00 mM) injecting into P(VBSC4A) (250 µM) in aqueous solution and (b) apparent reaction heat obtained from the integration of calorimetric traces.

DETAILED DESCRIPTION OF THE INVENTION

It should be understood that the detailed description and specific examples, while indicating aspects of the invention, are given by way of illustration only, since various changes and modifications within the spirit and scope of the invention will become apparent to those skilled in the art. One skilled in the art, based upon the description herein, may utilize the present invention to its fullest extent. The following specific embodiments are to be construed as merely illustrative, and not limitative of the remainder of the disclosure in any way whatsoever.

Except as defined herein, all the technical and scientific terms used herein have the same meaning as commonly understood by one of ordinary skill in the art to which the invention belongs.

The terms "a", "an" and "the" refers to "one or more" when used in the subject specification, including the claims. Thus, for example, reference to "a compound" may include a plurality of such compounds.

It should also be noted that the term "or" is generally employed in its sense including "and/or" unless the content clearly dictates otherwise.

The following abbreviations or terms are used herein:
AIBN: Azobis-Isobutyronitrile
ATRP: Atom Transfer Radical Polymerization
CV: Cyclic Voltammetry
DCE: Dichloroethene
FTIR: Transform Infrared Spectroscopy
GPC: Gel Permeation Chromatography
IR: Infrared
ITC: Isothermal Titration Calorimetry
LC/MS: Liquid Coupled Mass Spectroscopy
MP: Peak Molecular Weight
MV: Methyl Viologen
NMR: Nuclear Magnetic Resonance
PDI: Polydispersity index
P(VBC4A): Poly (25-(4-vinylbenzyl)-26, 27, 28-hydroxy-calix[4]arene)
P(VBSC4A): Poly (p-sulfo, 25-(4-vinylbenzyl)-26, 27, 28-hydroxy-calix[4]arene)
THF: Tetrahydrofuran
TMS: Tetramethyl silane
UV: Ultraviolet
XPS: X-ray Photoelectron Spectroscopy A new polystyrene-based pendant functionalized sulfonated calixarene material was synthesized. The number in [ ] denotes the number of calix units. This number can be 4, 6, 8, 10 or more. Ring structures other than calixarene can be used.

A styrene based water soluble polymer containing pendant sulfonated calixarene groups has been synthesized by using free radical polymerization combined with polypolymerization sulfonation.

Figure 2:
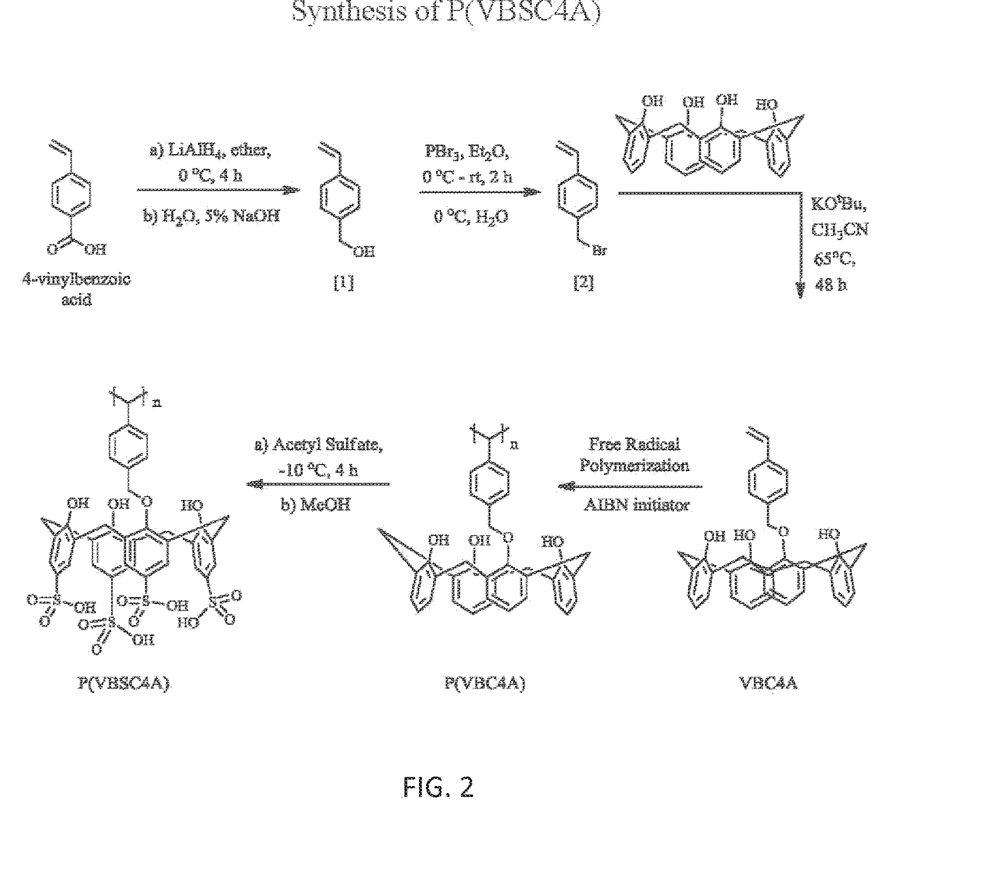
FIG. 2 shows a reaction scheme for preparation of electro-responsive P(VBSC4A).

FIG. 2 shows the synthetic approach utilized to prepare the electro-responsive polymer. This approach can be used to prepare polystyrenes with calix units.

The monomer is prepared by using a three step reaction scheme. The monomer is polymerized by free radical polymerization. After polymerization, the wide rim of the calix[ ]arene ring is sulfonated.

In an aspect of the invention polymer is prepared by: 1) reducing 4-vinyl benzoic acid to alcohol, 2) formation of bromide by the Appel reaction and 3) synthesis of the respective ether by Williamson O-alkylation reaction with calix[ ]arene.

The monomer is polymerized by AIBN free radical polymerization. After polymerization, the wide rim of the calyx[ ]arene ring was sulfonated. The para position of each phenyl group of calixarene rings was sulfonated.

In another aspect of the invention, polymers can be synthesized by Atom Transfer Radical Polymerization (ATRP) followed by sulfonation.

The electro-responsive poly(VBSC4A) based on homoditopic calixarene was constructed based upon the synthetic approach shown in FIG. 2.

The monomer, 25-(4-vinylbenzyl)-26,27, 28-hydroxy-calix[4]arene(VBC4A) is prepared by using a three step reaction scheme. VBC4A is polymerized by free radical polymerization. After polymerization, the wide rim of the calix[4]arene ring was sulfonated.

In an aspect of the invention 25-(4-vinylbenzyl)-26,27, 28-hydroxy-calix[4]arene(VBC4A) is prepared by: 1) reducing 4-vinyl benzoic acid to alcohol, 2) formation of bromide by the Appel reaction and 3) synthesis of the respective ether by Williamson O-alkylation reaction with calix[4]arene.

VBC4A is polymerized by AIBN free radical polymerization. After polymerization, the wide rim of the calyx[4] arene ring was sulfonated. The para position of each phenyl group of calixarene rings was sulfonated.

In another aspect, Polymerization was accomplished by AIBN initiated free radical polymerization technique to form P(VBC4A). P(VBC4A) was subsequently reacted with acetyl sulfate to afford the sulfonated polymer.

In another aspect of the invention, polymers can be synthesized by Atom Transfer Radical Polymerization (ATRP) of 25-(4-vinylbenzyl)-26, 27, 28-hydroxy-calix[4] arene (VBC4A) followed by treatment with acetyl sulfate.

Figure 3:
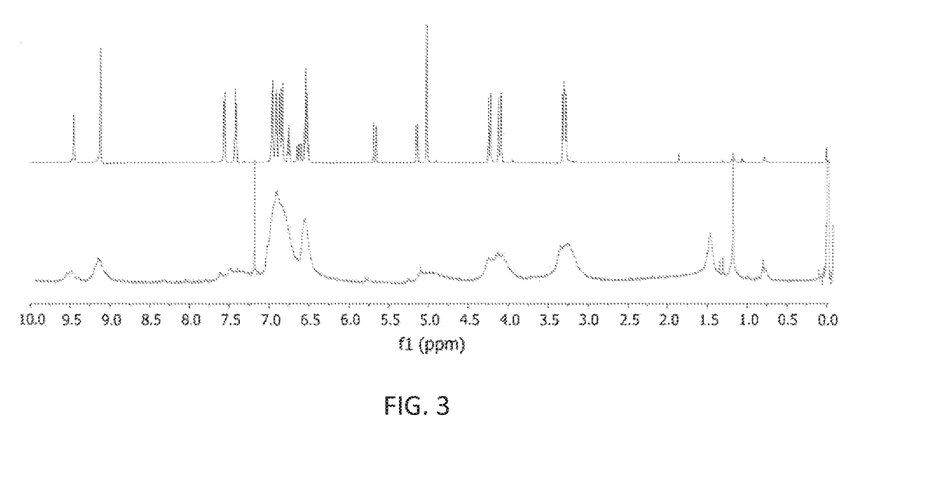
FIG. 3 shows a comparison of $^1$H NMR peaks between (a) Monomer VBC4A (upper scan) and (b) P(VBC4A) (lower scan).

VBC4A and P(VBC4A) have been characterized by $^1$D and $^2$D NMR and LC/MS (data not shown). FIG. 3(a) shows the $^1$H NMR of VBC4A (upper scan) and FIG. 3(b) P(VBC4A) (lower scan). The polymer shows proton resonances in regions similar to the monomer but are substantially broadened. This is true for all the peaks except the vinyl proton resonance peaks observed at 5.3 and 5.7 ppm in the monomer that are not observed in the polymer. The lack of these two proton peaks confirms that the monomer has been converted to a polymer.

Figure 4:
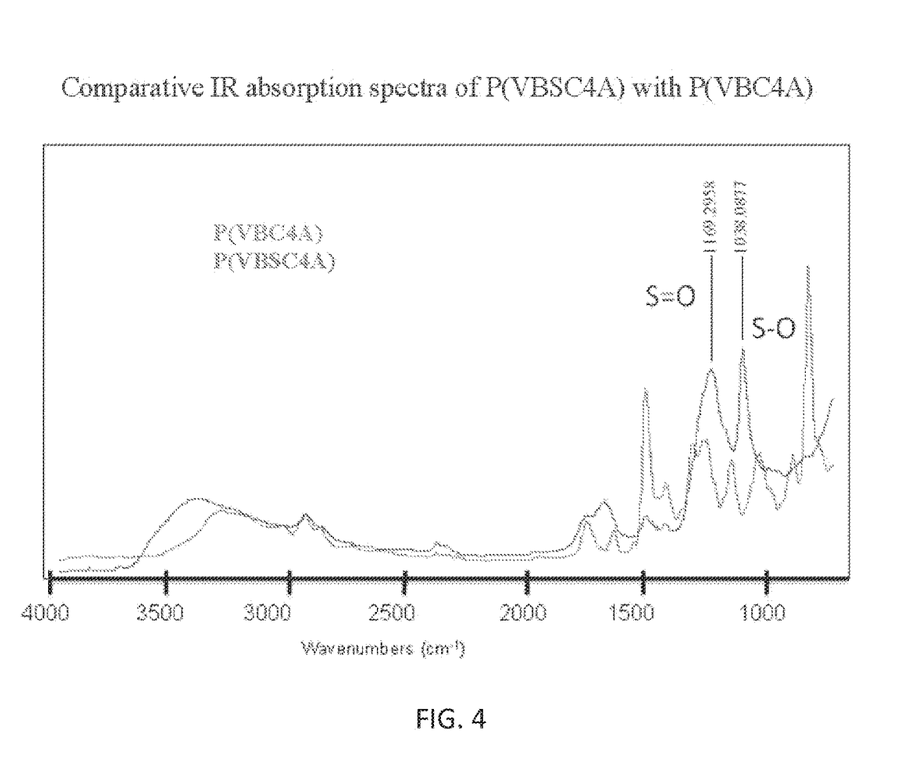
FIG. 4 shows comparative IR absorption spectra of P(VBSC4A) with P(VBC4A).

To confirm the success of polymer derivatization, the FTIR spectra of unsulfonated (P(VBC4A)) and sulfonated (P(VBSC4)) polymers were compared (see FIG. 4). The strong sulfur/oxygen stretching vibration observed at 1169 to 1038 cm$^{-1}$ is characteristic of combined S=O and S—O stretches. This band region is greatly enhanced in the spectra of P(VBSC4A) as compared to the spectra of the unsulfonated analog. Other features of the spectra are the prominent broad band at 3162-3400 cm$^{-1}$ indicative of hydroxyl (OH) groups.

Molecular weights were evaluated by Gel Permeation Chromatography (GPC) using a polystyrene standard kit for molecular weight elution volume calibration.

Figure 5:
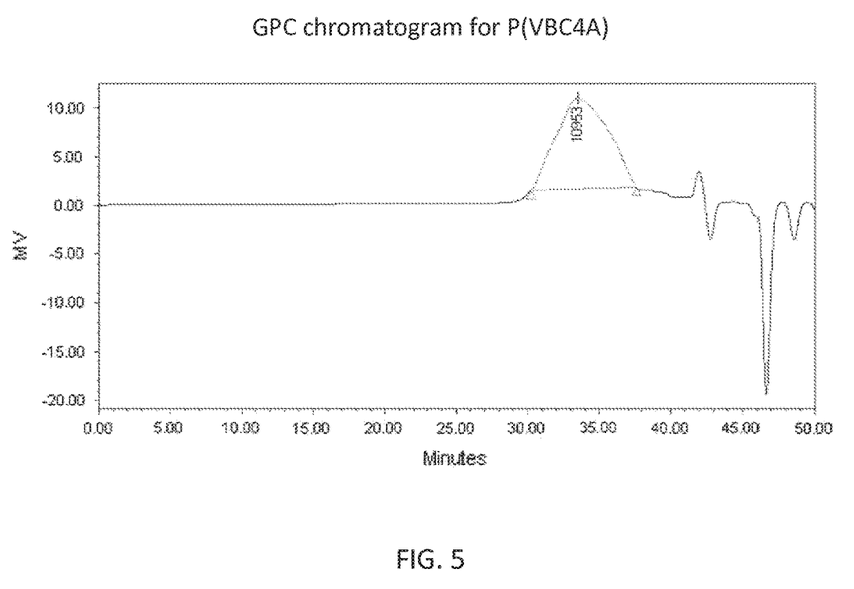
FIG. 5 shows GPC chromatogram for P(VBC4A).

A broad peak was observed at 33.48 minutes retention time (FIG. 5). The chromatogram of P(VBC4A) gives Mn, Mw, MP and PDI as 7090, 11700, 10900 Daltons and 1.65 respectively.

Figure 6:
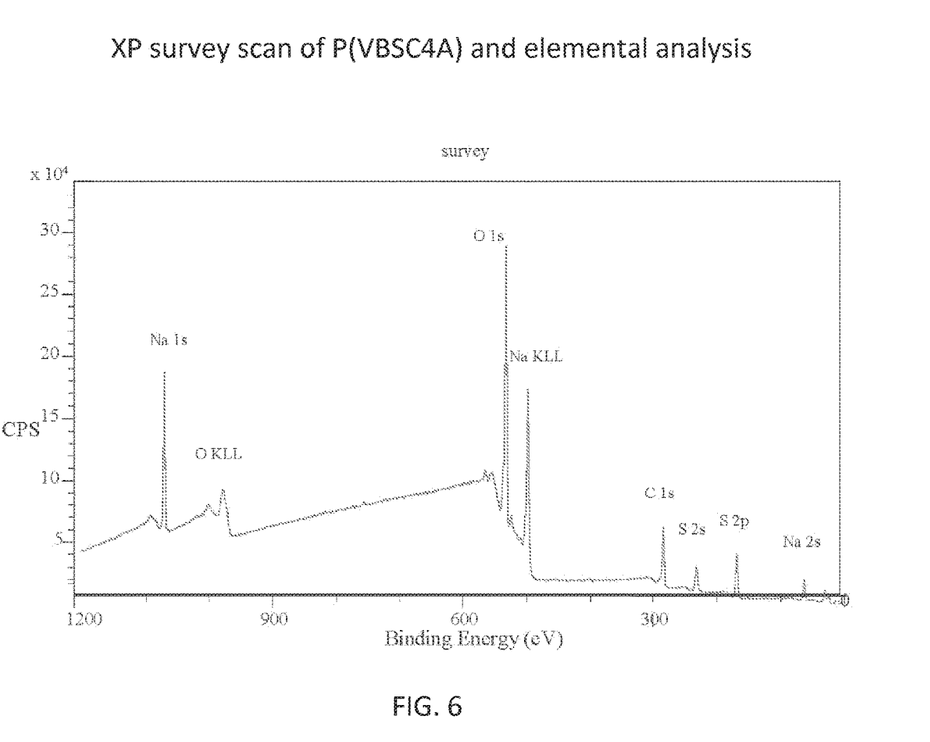
FIG. 6 shows XP scan of P(VBSC4A) and elemental analysis. The scan shows Carbon 1s, Oxygen 1s, Sulfur 2p, and Ca 2p binding energies.
Figure 8:
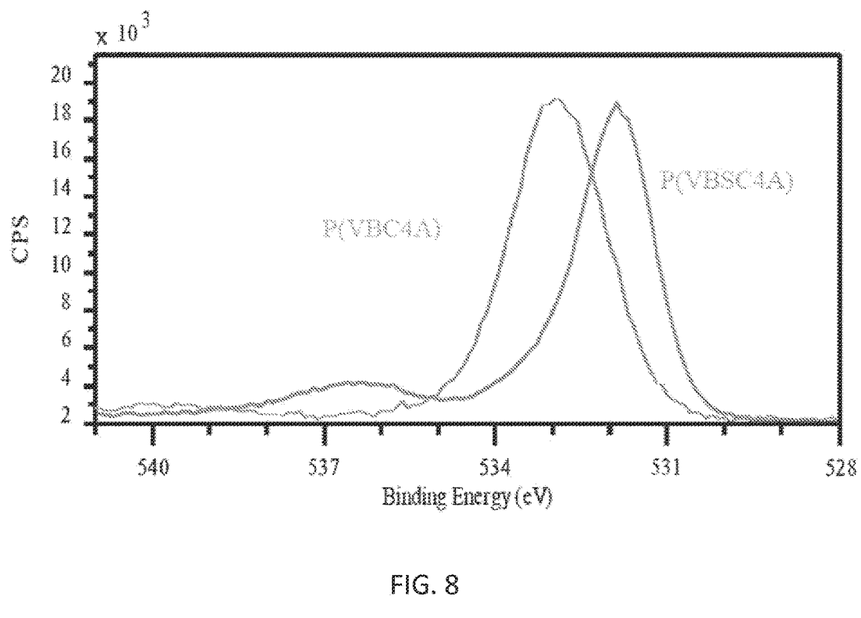
FIG. 8 shows relative O 1s peaks of sulfonated P(VBSC4A) and non-sulfonated P(VBC4A) polymers (XPS).

The degree of sulfonation of the calixarene ring of the polymer was analyzed by subjecting films of the material by XPS (FIG. 6). Residual sodium was observed possibly from the residual counter ions in the dilute sodium hydroxide workup. It is shown that the oxygen binds to different elements in the sulfonated polymer such as O—Na, O—S and shows an asymmetrical fused peak on O 1s scan ranging from 528-531 eV and 531.5-532.5 eV respectively. The unsulfonated polymer contains O—H bonding and the characteristic peak was observed in between O—Na and O—S peak which matches with Table 1 and FIG. 8. The percentage of the other atoms is reasonable if one considers remaining water molecules that exist in the final hydrophilic material despite rigorous drying attempts.

TABLE 1

Percent elemental composition of P(VBSC4A) theory vs experiment (XPS).

| Element | O 1 s (%) | C 1 s (%) | Na 1 s (%) | S 2 p (%) |
|---|---|---|---|---|
| Theoretical * | 38.88 | 34.84 | 16.22 | 10.06 |
| Experimental | 39.24 | 34.15 | 16.41 | 10.21 |

* P(VBSC4A) 8Na 15H$_2$O

Theoretically calculated element percentages for sulfonated VBC4A (P(VBSC4A)) are close to the experimental values of elemental analysis by XPS when accounting for residual water molecules that are associated with the films (J. F. Moulder, et al., Handbook of X-ray Photoelectron Spectroscopy, Physical Electronics Inc., 1993, see Table 2). The sulfur percentages determined experimentally are reasonably identical to those calculated, indicating complete sulfonation on the lower rim of the calix[4]arene pendent group.

TABLE 2

Comparison of O 1s peaks from different oxygen bonding with metal, hydrogen and sulfur (adapted from book (Moulder (1993), Hand book of X-ray Photoelectron Spectroscopy).

| eV | 528 | 529 | 530 | 531 | 532 | 533 |
|---|---|---|---|---|---|---|
| Metal oxide | ├─────────┼─────────┤ | | | | | |
| hydroxide | | | | ├───┤ | | |
| Sulfates | | | | | ├─────────┤ | |

Figure 1:
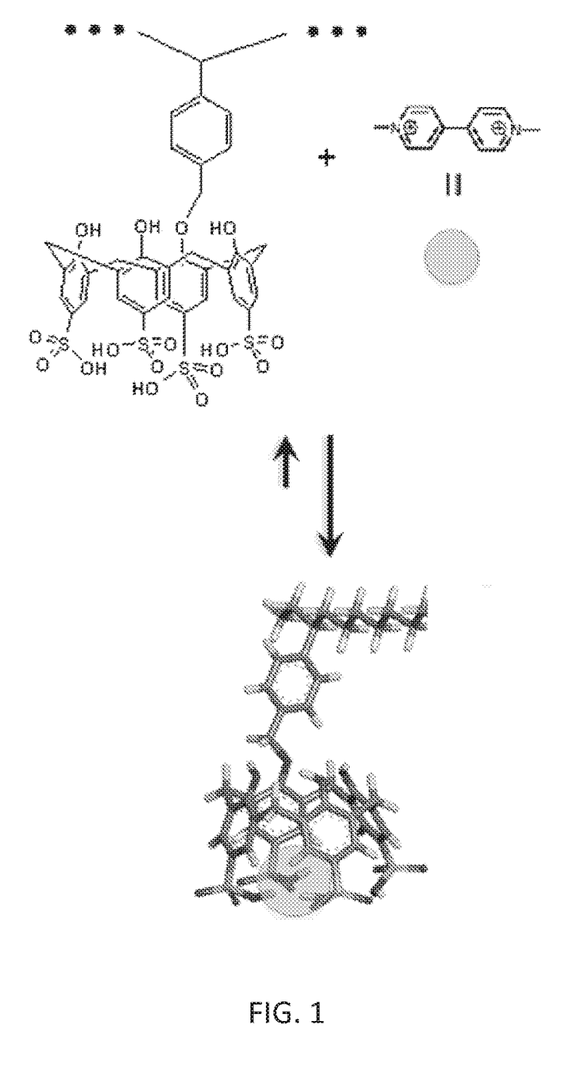
FIG. 1 shows a schematic representation of formation of host-guest complexation between viologen and polystyrene-based pendant functionalized sulfonated calix[4]arene.
Figure 10:
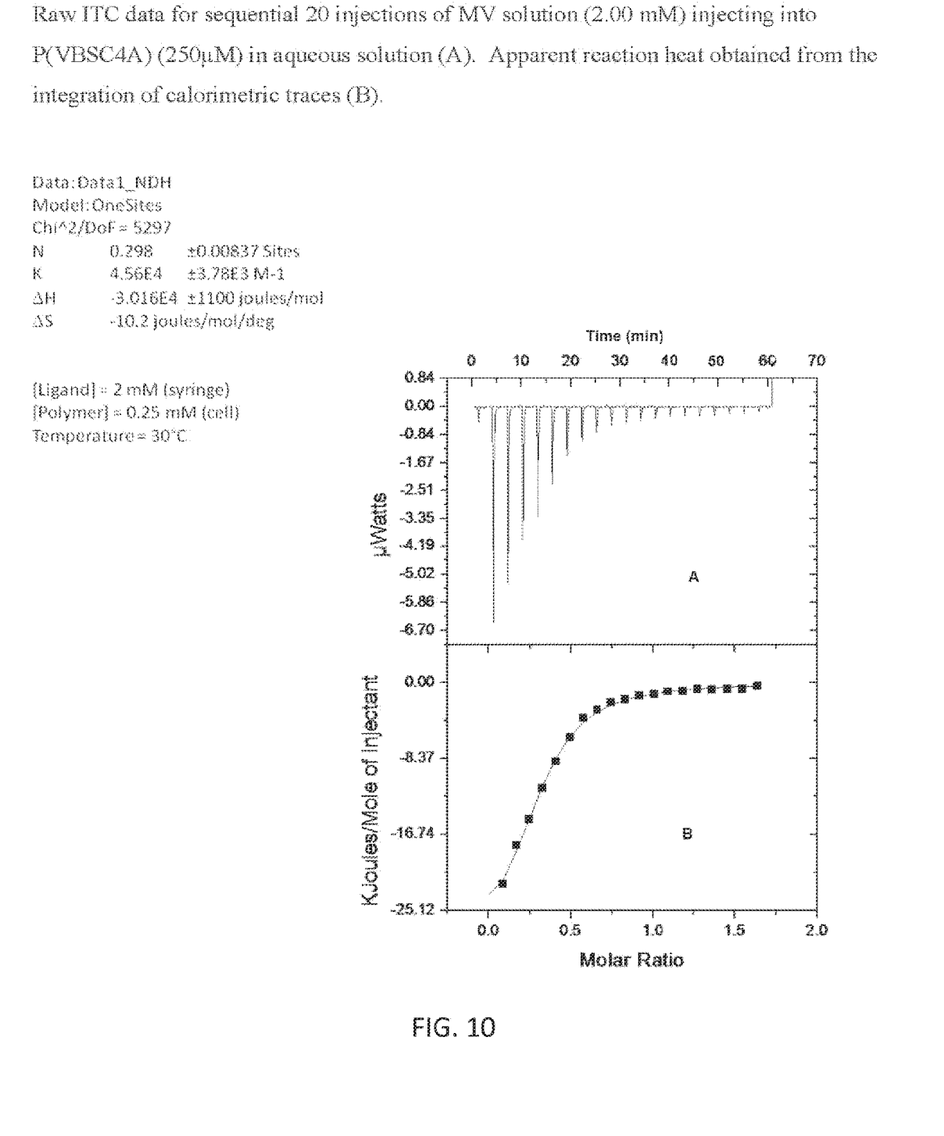

The polymer [P(VBSC4A)] reversibly responded to electrochemical stimulus in a controlled manner by incorporation or dissociation of guest molecules. Its complexation with methyl viologen (MV), as a guest molecule, can be reversibly controlled by electrochemical stimuli (see FIG. 1). The complexation properties of P(VBSC4A) were investigated by fluorescence measurements. P(VBSC4A) shows a broad emission band that is strongest at 320 nm when excited at 210 nm. There is also a less intense emission band at ~300 nm. This band at 300 nm was largely quenched when MV was added to P(VBSC4A) in solution (20 μM) (FIG. 10). MV is a polynuclear aromatic compound and P(VBSC4A) is largely composed of benzene rings, thus the driving force of the complex formation may be π-π interactions.

ITC experiments supply the quantitative information for the host-guest complexation between P(VBSC4A) and MV. As shown in FIG. 10, the association constant was obtained as $4.56 \times 10^4$ M$^{-1}$ with an average 0.2% error in predicting a 3:10 complexation case of P(VBSC4A) with MV (ΔH=−30.16 kJ/mol; ΔS=−10.2 joules/mol/deg). The complexation appears to be thermodynamically favorable as both the enthalpy and entropy are accompanied with negative changes upon association. The resulting negative Gibbs free energy of formation for the complex pushes the reversible assembly/disassembly equilibrium toward formation, an energetic state also observed by in the 1:1 complexation case of SC4A with bi-methyl viologen. (D. S. Guo, et al., Highly effective binding of methyl viologen dication and its radical cation by p-sulfonatocalix[4,5]arenes, Journal of Organic Chemistry 72 (2007) 7775-7778.)

Figure 11:
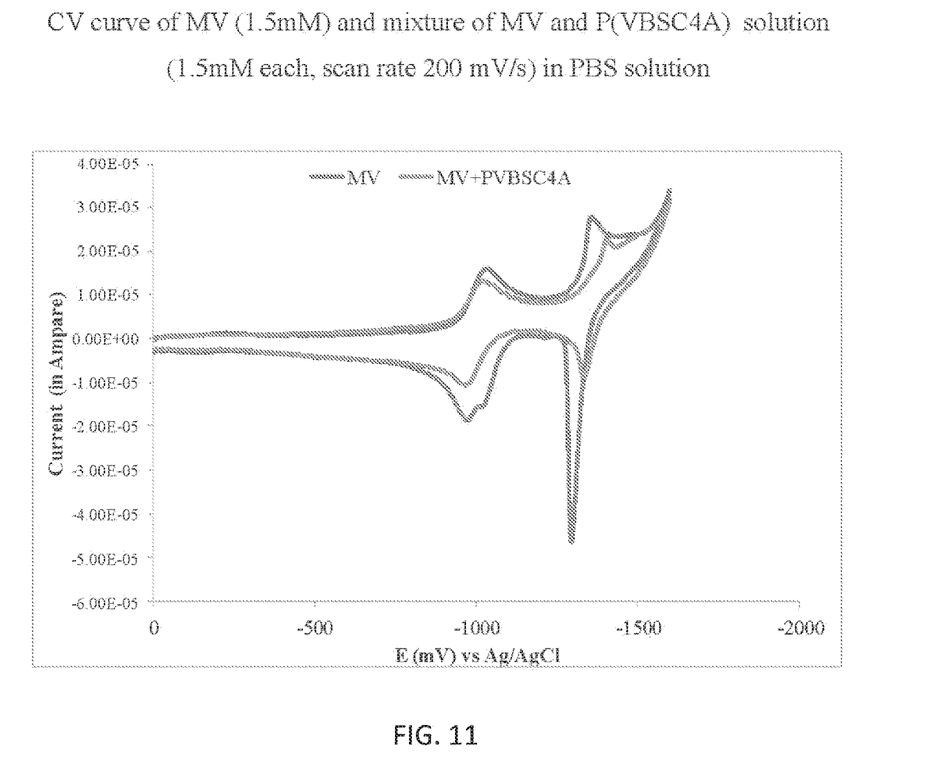
FIG. 11 shows CV curve of MV (1.5 mM) and P(VBSC4A) solution (1.5 mM each, scan rate 200 mV/s) in PBS solution.

The electrochemical sensitivity of the P(VBSC4A) was further studied by cyclic voltammetry (CV). Typical cyclic voltammograms of MV obtained in the absence and presence of P(VBSC4A) are shown in FIG. 11. It is well documented (and observed here) that free MV$^{2+}$ undergoes two consecutive one-electron reduction processes to its neutral form MV$^0$. However, the voltammogram of MV$^{2+}$ in the presence of P(VBSC4A) undergoes a noticeable shift in the peak potentials and a marked decrease in the current levels.

For the first reduction potential (MV$^{2+}$/MV$^{+X}$), the reversible shape of the half wave potential is retained in the presence of P(VBSC4A)—just shifted to a more positive value by $\Delta E_{1/2} \approx 16$ mV compared to MV alone. This shift suggests that the species is slightly easier to be reduced. In contrast, for the second reduction potential (MV$^{+X}$/MV$^0$) the half-wave potential shifts to more negative values in the presence of P(VBSC4A) by $\Delta E_{1/2} \approx 46$ mV. This shift indicates that MV cation radical is included into the cavity of P(VBSC4A) while the negative nature of the shift indicates the species is more difficult to reduce.

The two peaks of MV were observed at ca. −1296 mV and −976 mV. These two waves were repeatedly observed even after cleaning the electrodes and degassing the solution. These peaks belong to the free radical accumulated in oxidation process. H. J. Kim, et al., Inclusion of methylviologen in cucurbit[7] uril, Proc Natl Acad Sci USA 99 (2002) 5007-5011. Upon complexation with P(VBSC4A), the second reduction peak undergoes a significant negative shift, while the corresponding re-oxidation peak shifts by about the same amount (42 mV). Morever, the first re-oxidation peak is now one peak located at −963 mV.

Taken together, the shifts in the half-wave potentials indicate relative strength of the association between the host and the guest MV in its different redox states. Thus, the cyclic voltammetry results show that P(VBSC4A) prefers the charged species over the neutral species of $MV^0$ as a guest.

Unlike the supramolecular calixarene polymer reported earlier (D. S. Guo, S. Chen, H. Qian, H. Q. Zhang, Y. Lui, Chem. Coramun. 46 (2010) 2620-2622) the backbone of the polymer chain is kinetically less labile and thermodynamically more stable yet accommodating to the dynamic interaction of a guest molecule The calixarene polymer of this invention may be used for reversibly binding guest molecules. The calixarene polymer of this invention may be used for drug deliver or chemical sensor devices.

The invention will be further explained by the following illustrative examples that are intended to be non-limiting.

EXAMPLES $^1H$ and $^{13}C$ NMR spectra were recorded in deuterated chloroform (unless otherwise noted) on a Varian spectrometer operating at 500 MHz using tetramethylsilane (TMS) as a reference.

IR spectra were recorded on a Travel IR HCl by Sens IR technologies. An Applied Biosystems Voyager-DE PRO-mass spectrometer equipped with a nitrogen laser (337 nm) was used to collect MALDI mass spectra data.

Molecular weights were also evaluated by a Waters Alliance GPC System, Waters 2695 Separations Module and Waters 2414 Refractive Index Detector (Waters Associates Inc., Milford, Mass.).

Approximately 20-30 mg of sample was dissolved in THE and the GPC analysis was performed at 35° C. using a polystyrene standard kit for molecular weight elution volume calibration. 4-vinylbenzoic acid was used as received from VWR. All other solvents and reagents were used as supplied from either Fisher Scientific or VWR. All solvents were purchased in the anhydrous form.

Example 1

Synthesis of 4-vinylbenzyl alcohol

A solution of 4-vinylbenzoic acid (500 mg, 3.37 mmol) in Et$_2$O (25 mL) was added dropwise to a 0° C. slurry of LiAlH$_4$ (758 mg, 19.97 mmol) in THF (80 mL) (K. S. Bloome, et al., Palladium-catalyzed Heck-type reactions of alkyl iodides, J Am Chem Soc 133 (2011) 20146-20148, 2011) The reaction mixture was warmed to room temperature and stirred for one hour. The reaction was quenched via the following workup; 256 µL water added slowly, followed by the addition of 512 µL of 10 wt % NaOH solution, and then 768 µL water. The mixture was stirred vigorously until a white solid was formed. The crude reaction mixture was filtered, and the supernatant was dried (anhydrous Na$_2$SO$_4$), and concentrated in vacuo. The resulting oil was purified by silica gel column chromatography using an eluant of Hexane:EtOAc, (4:1) to provide alcohol 1 (shown in FIG. 2) (280 mg, 62%) as a colorless oil.

$^1$H NMR (CDCl3, 500 MHz) δ: 4.66 (s, 2H), 5.24 (d, J=11.5 Hz, 1H) 5.73 (d, J=18.5 Hz, 1H) 6.69-6.75 (dd, J=11.0, 6.5 Hz, 1H) 7.31 (d, J=8.0 Hz, 2H) 7.39 (d, J=8.0 Hz, 2H).

Example 2

Synthesis of 4-Vinylbenzyl bromide

Using a reaction scheme adapted from O. Shimomura, et al, Synthesis and application of polytetrahydrofuran-grafted polystyrene (PS-PTHF) resin supports for organic synthesis, Tetrahedron 61 (2005) 12160-12167, phosphorous tribromide (PBr$_3$) (18.4 g, 6.4 ml, 68 mmol) dissolved in ethyl ether (10 ml) was added to 4-vinylbenzyl alcohol (5.9 g, 44.3 mmol) in Et$_2$O (500 ml) at 0° C. under N$_2$. After 1 hour, additional PBr$_3$ (18.4 g, 6.4 ml, 68 mmol) was added. The reaction mixture was stirred for 1 hour at room temperature and subsequently cooled to 0° C. Water (100 ml) was slowly added. The solution was extracted with Et$_2$O, and the Et$_2$O layer was washed with aqueous NaHCO$_3$, brine and dried with MgSO$_4$. The crude product was purified by silica gel column chromatography using a hexane:EtOAc, (70:30) eluent system to obtain product vinyl benzyl bromide. $^1$H NMR (CDCl$_3$, 500 MHz) δ: 4.48 (s, 2H), 5.26 (d, 1H) 5.76 (d, 1H) 6.69-6.75 (q, 1H) 7.32 (d, 2H) 7.41 (d, 2H). UV-vis [chloroform, $\lambda_{max}(\varepsilon)$]: 215, 260.

Example 4

Synthesis of 25-(4-vinylbenzyl)-26, 27, 28-hydroxy-calix[4]arene (VBC4A)

Calix[4]arene (1 g, 2.36 mmol) and potassium tertbutoxide (528 mg, 4.71 mmol) were dissolved in anhydrous acetonitrile (10 ml) by stirring at 65° C. under N$_2$. After 1 h, 4-vinyl benzyl bromide (460 mg, 2.35 mmol) was added and the mixture refluxed for 48 h. The reaction mixture was concentrated under vacuum. The resulting solid was dissolved in DCM, washed with 1M HCl, D1 water, brine and dried over anhydrous Na$_2$SO$_4$. The crude product was purified by silica gel column chromatography using Hexane:EtOAc (90:10) providing monomer VBC4A as a white crystalline solid (20% yield). $^1$H NMR (CDCl$_3$, 500 MHz) δ: 3.27-3.32 (dd, J=10.0, 5.0 Hz, 4H, Ar—CH$_2$—Ar), 4.09 (d, J=15.0 Hz, 2H, Ar—CH$_2$—Ar), 4.22 (d, J=10.0 Hz, 2H, Ar—CH$_2$—Ar), 5.02 (s, 2H, —O—CH$_2$), 5.13 (d, J=15.0 Hz, 1H), 5.66 (d, 15.0 Hz, 1H), 6.51-6.55 (dd, J=5.0, 10 Hz, 3H, Ar—H), 6.59-6.65 (dd, J=15.0, 5.0 Hz, 1H, C—H) 6.74 (t, J 5.0 Hz, 1H, Ar—H), 6.83-6.87 (dd, J=10.0, 5.0 Hz, 4H, Ar—H), 6.90 (d, J=10.0 Hz, 2H, Ar—H), 6.95 (d, J=10.0 Hz, 2H, Ar—H), 7.41 (d, J=5.0 Hz, 2H, Ar—H), 7.55 (d, J=10.0 Hz, 2H, Ar—H), 9.12 (s, 2H, Ar—OH), 9.45 (s, 1H, Ar—OH); $^{13}$C NMR (CDCl$_3$, TMS, 125 MHz) δ: 32.11 (Ar—CH$_2$—Ar), 79.18 (O—CH$_2$), 114.9 (=CH$_2$), 121.14-138.49 (Ar), 136.6 (—CH), 149.36 (Ar—OH), 151.46 (Ar—O—); UV-Vis [DCM, $\lambda_{max}(\varepsilon)$]: 230 and 254 nm; ESI/APCI-MS: m/z 540.1 [M+H].

Example 5

Preparation of Poly(25-(4-vinylbenzyl)-26, 27, 28-hydroxy-calix[4]arene) (P(VBC4A))

Monomer VBC4A (1 g, 1.85 mmol) and azobisisobutyronitrile (AIBN) (6.07 mg, 0.037 mmol) were dissolved in 10 mL of THF and stirred at 60° C. under N$_2$ for 48 hrs. The reaction mixture was purified by silica gel flash column and recrystallized in MeOH providing P(VBC4A), a white amorphous white powder with 70% yield. $^1$H NMR (CDCl$_3$, 500 MHz) δ: 1.26-1.85 (broad 2H+1H, —CH$_2$—CH—Ar—), 3.00-3.60 (broad 4H, Ar—CH$_2$—Ar), 3.85-4.45 (broad 4H, Ar—CH$_2$—Ar), 4.65-5.20 (broad, 2H, —O—CH$_2$—), 6.25-7.80 (broad, 16H, Ar—H), 9.10-9.85 (broad, 3H, Ar—OH); $^{13}$C NMR (CDCl$_3$, TMS, 125 MHz) δ31.80 (Ar—CH$_2$—Ar), 40.35 (—CH$_2$—C—Ar—), 79.10

(OCH$_2$), 120.93-130.35 (Ar), 134.35 (—CH—Ar—), 149.07 (Ar—OH), 151.14 (Ar—O—); UV-vis [DCM, $\lambda_{max}$ (ε)]: 230, 276.

Example 6

Poly(p-sulfo, 25-(4-vinylbenzyl)-26, 27, 28-hydroxy-calix[4]arene) (P(VBSC4A))

Acetyl sulfate was freshly prepared by adding acetic anhydride (1.77 mL, 18.74 mmol) to the DCE (10 mL) at −10° C. After 5 mins, 95% sulfuric acid (1 mL, 18.77 mmol) was added to the DCE solution at −10° C., stirred and allowed to equilibrate at room temperature. Subsequently, acetyl sulfate (3.57 mL freshly prepared) was added to the poly(25-(4-vinylbenzyl)-26, 27, 28-hydroxy-calix[4]arene) (P(VBC4A)) solution in DCE (50 mL) (1:6 molar ratio, polymer:acetyl sulfate) at −10° C. and stirred for 4 h. The reaction mixture was filtered and the residue was dissolved in MeOH. The MeOH solution was washed with sodium hydroxide solution (10% aqueous) to neutralize the excess sulfuric acid and subsequently dialyzed (<2000 MW cut off membrane) for 2 days and lyophilized until dry. The dry purple amorphous powder was obtained in 10% yield. $^1$H NMR (D$_2$O, 500 MHz) δ: 1.10-2.50 (broad 3H, —CH$_2$—CH—Ar—), 3.25-3.64 (broad 4H, Ar—CH$_2$—Ar), 3.65-4.03 (broad 4H, Ar—CH$_2$—Ar), 4.20-4.46 (broad, 2H, —O—CH$_2$—), 6.74-7.89 (broad, 16H, Ar—H); $^{13}$C NMR (CD$_3$OH, TMS, 125 MHz) δ: 21.03-22.01 (Ar—CH$_2$—Ar), 31.33 (Ar—CH$_2$—Ar), 32.99 (Ar—CH$_2$—Ar), 38.42 (—CH$_2$—C—Ar—), 64.33 (O—CH$_2$), 124.97-130.49 (Ar), 135.08 (—CH—Ar—), 148-152 (Ar—O(H)); UV-vis [DCM, $\lambda_{max}$(ε)]: 210 nm.

Example 7

Characterization of Poly(VBSC4A)

A. X-Ray Photoelectron Spectrometer (XPS)

XPS was performed with a Kratos Analytical Axis Ultra Photoelectron spectrometer using monochromatic Al source, emission 10 mA and starting with 1200 eV energy. The pressure in the analysis chamber was 1×10$^{-8}$ torr. A spectra was obtained as a function of binding energy in eV. Casa XPS software was used for data processing, (See FIG. 6).

B. Absorption and Emission Spectroscopy

Figure 7:
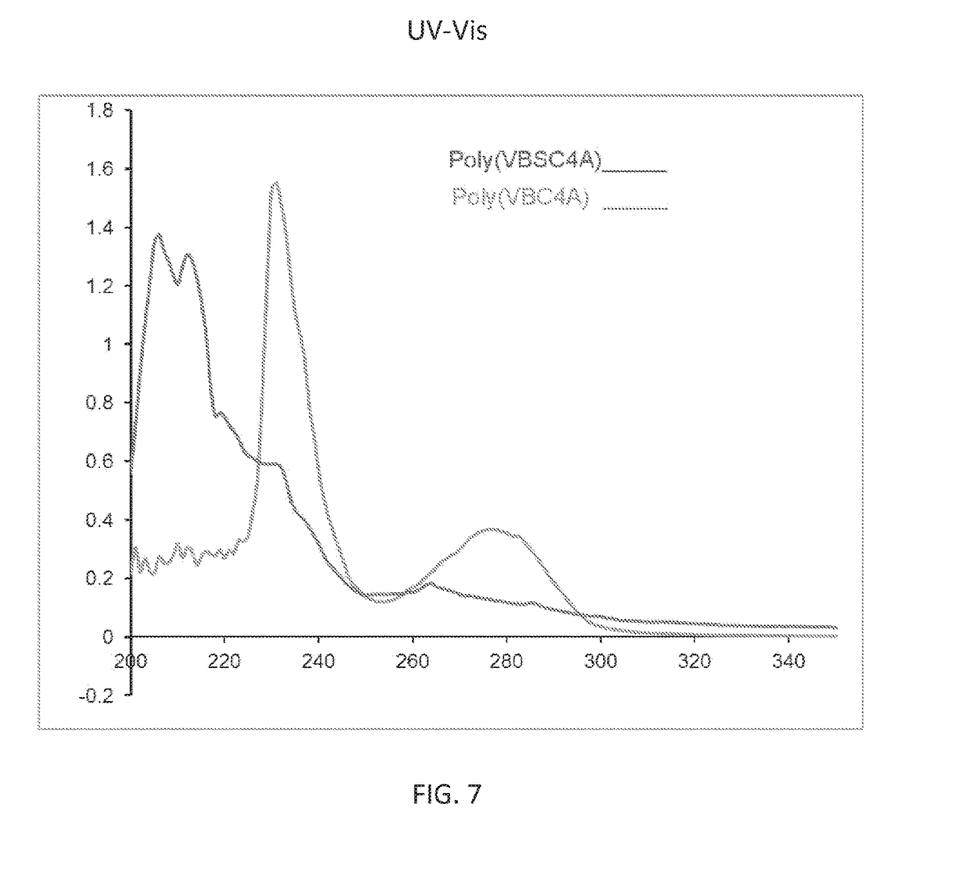
FIG. 7 shows UV-Vis absorbance before and after sulfonation (150 µM in DCM) (P (VBC4A) and P (YBSC4A)).

Absorption spectra were measured with a Hewlett-Packard Model 8453 UV-Vis spectrophotometer with HP Vectra Workstation. The fluorescence spectra were observed on a Perkin Elmer LS 55 Fluorescence Spectrophotometer at ambient temperature. In both absorbance and emission spectra, the samples were prepared in PBS (0.1 M, pH7) and measurements were conducted in 1 cm path-length quartz cells. (See FIG. 7).

C. Isothermal Titration Calorimetry (ITC)

Figure 9:
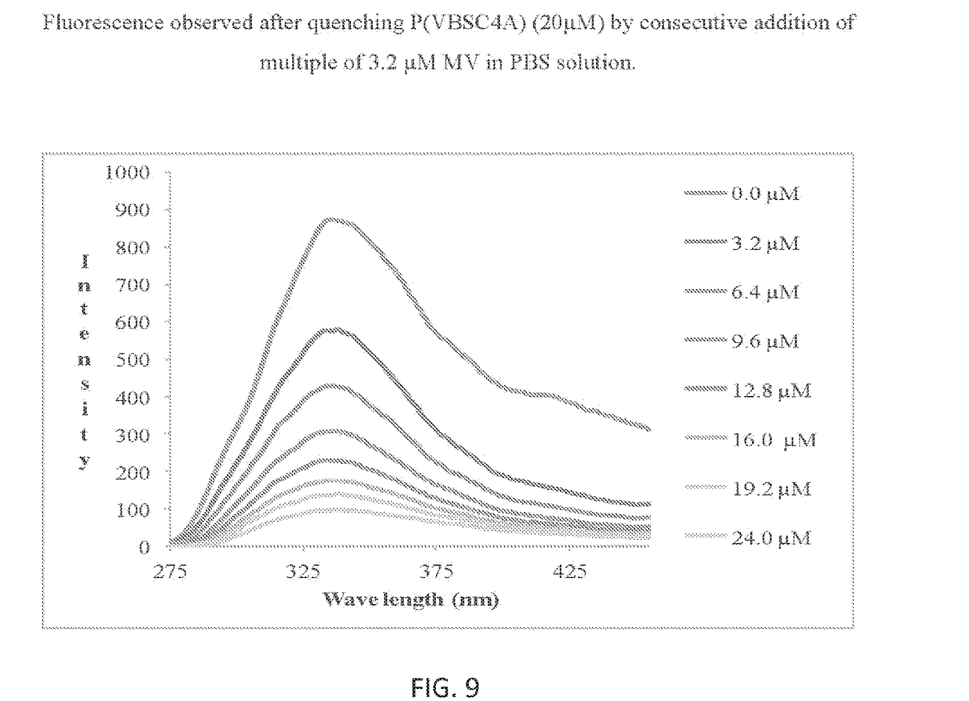
FIG. 9 shows fluorescence observed after quenching P(VBSC4A) (20 µM) by consecutive addition of multiple of 3.2 µM MV in PBS solution.

The formation constant and thermodynamic parameters for the inclusion of MV in P(VBSC4A) polymer were measured by the titration calorimetry method using a MicroCal iTC200 instrument. All solutions were prepared in phosphate buffer saline solution (0.1 M, pH 7). A solution of P(VBSC4A) (250 μM) was placed in the sample cell. As a 2.00 mM solution of MV was added in a series of 20 injections (3 μL each), the evolved heat was recorded. ITC experiments were performed at 30° C. The data were analyzed and fitted by using ORIGIN software (MicroCal). (See FIG. 9 (A) Raw ITC data for sequential 20 injections of MV solution (2.00 mM) injecting into polymer solution (250 μM). (B) Apparent reaction heat obtained from the integration of calorimetric traces. Cumulative heat of reaction obtained from the integration of calorimetric traces is displayed as a function of the injection number. The solid line is the least-squares fit to the experimental data of separate trials. $X^2$/DoF=5297; N=0.298±0.008 Sites.)

D. Cyclic voltammograms (CV) were recorded using a BAS potentiostat (CV-50W with C3 Cell Stand) interfaced to a personal computer and software supplied by the manufacturer. Ail experiments were conducted in phosphate buffer (pH 7.2, 0.1 M) at room temperature. A working volume of 5 mL was transferred to the cell by syringe immediately prior to the start of the experiment. A normal one compartment cell was utilized with a Pt disk working electrode (MF-2013, BAS), a Pt wire auxiliary electrode (MW-1032), and a Ag/AgCl reference electrode (MF-2052, BAS). All potentials are reported versus Ag/AgCl. Electrochemical potentials were converted to vacuum assuming the normal hydrogen electrode (NHE) to be at 4.7 eV versus vacuum with an additional +0.2 V potential difference between Ag/AgCl and NHE. Before each experiment, the cell was purged with N$_2$ for 5-10 min and a blanket of N$_2$ was maintained during the experiment. (See FIG. 11).

The invention claimed is:

1. A polymer (p-sulfo, 25-(4-vinylbenzyl)-26, 27, 28-hydroxy-calix[X]arene) where X is selected from 4, 6, 8, 10 or higher.

2. The polymer according to claim 1, wherein X is 4, 6, 8 or 10.

3. The polymer according to claim 1, wherein X is 4.

4. A polymer (25-(4-vinylbenzyl)-26, 27, 28-hydroxy-calix[X]arene) where X is selected from 4, 6, 8, or 10.

5. The polymer according to claim 4, wherein X is 4.

6. A method for preparing poly (p-sulfo, 25-(4-vinylbenzyl)-26, 27, 28-hydroxycalix[X]arene) according to claim 2 comprising the steps of a) reducing 4-vinylbenzoic acid to 4-vinylbenzyl alcohol; b) mixing 4-vinylbenzyl alcohol with a bromine to form 4-vinylbenzyl bromide; c) mixing 4-vinylbenzyl bromide with calix[X]arene to obtain 25-(4-vinylbenzyl)-26, 27, 28-hydroxy-calix[X]arene; d) mixing 25-(4-vinylbenzyl)-26, 27, 28-hydroxy-calix[X]arene and azobisisobutyronitrile to obtain poly (25-(4-vinylbenzyl)-26, 27, 28-hydroxy-calix[X]arene) and e) adding a sulfonating compound to poly (25-(4-vinylbenzyl)-26, 27, 28-hydroxy-calix[X]arene) where X is 4, 6, 8 or 10.

7. A method for preparing poly (p-sulfo, 25-(4-vinylbenzyl)-26, 27, 28-hydroxycalix[X]arene) according to claim 2 comprising the steps of:
   a) mixing 25-(4-vinylbenzyl)-26, 27, 28-hydroxy-calix[X]arene and azobisisobutyronitrile to obtain poly (25-(4-vinylbenzyl)-26, 27, 28-hydroxycalix[X]arene) and
   b) adding a sulfonating agent to poly (25-(4-vinylbenzyl)-26, 27, 28-hydroxy-calix[X]arene), where X is 4, 6, 8 or 10.

8. The method according to claim 6 wherein X is 4.

9. The method according to claim 6 wherein the sulfonating compound is acetyl sulfate.

10. A monomer 25-(4-vinylbenzyl)-26, 27, 28-hydroxy-calix[4]arene.

11. The polymer according to claim 1 that reversibly binds a guest molecule.

12. The polymer according to claim 11, wherein the guest molecule is methyl viologen (MV).

13. The polymer according to claim 1 that is sensitive to electrical stimuli.

14. An electrochemically-responsive system comprising the polymer according to claim 1 wherein sulfonated calixarene units are on a polystyrene backbone.

15. A method for reversible binding a guest molecule comprising applying an electrochemical stimulus to the polymer of claim 1 to incorporate or dissociate the guest molecule.

16. The method according to claim 7 wherein the sulfonating compound is acetyl sulfate.

17. The polymer according to claim 4 that reversibly binds a guest molecule.

18. The polymer according to claim 4 that is sensitive to electrical stimuli.

19. An electrochemically-responsive system comprising the polymer according to claim 4 wherein sulfonated calixarene units are on a polystyrene backbone.

20. A method for reversible binding a guest molecule comprising applying an electrochemical stimulus to the polymer of claim 4 to incorporate or dissociate the guest molecule.

* * * * *